US010434203B2

(12) United States Patent
Averett et al.

(10) Patent No.: US 10,434,203 B2
(45) Date of Patent: Oct. 8, 2019

(54) REDUCTION OF INFECTIONS IN HEALTHCARE SETTINGS USING PHOTOCATALYTIC COMPOSITIONS

(71) Applicant: WELL Shield LLC, Boca Raton, FL (US)

(72) Inventors: Stewart Benson Averett, Lighthouse Point, FL (US); Devron R. Averett, Berkley, CA (US)

(73) Assignee: WELL Shield LLC, Boca Raton, FL (US)

( * ) Notice: Subject to any disclaimer, the term of this patent is extended or adjusted under 35 U.S.C. 154(b) by 263 days.

(21) Appl. No.: 15/263,925

(22) Filed: Sep. 13, 2016

(65) Prior Publication Data

US 2016/0375164 A1 Dec. 29, 2016

Related U.S. Application Data

(63) Continuation of application No. 14/745,592, filed on Jun. 22, 2015, now abandoned.
(Continued)

(51) Int. Cl.
*A61L 2/08* (2006.01)
*B01J 23/06* (2006.01)
(Continued)

(52) U.S. Cl.
CPC .............. *A61L 2/088* (2013.01); *B01J 23/06* (2013.01); *B01J 35/004* (2013.01);
(Continued)

(58) Field of Classification Search
CPC ..................................................... A61L 2/088
(Continued)

(56) References Cited

U.S. PATENT DOCUMENTS 4,882,166 A 11/1989 Graham et al.
6,387,844 B1 5/2002 Fujishima et al.
(Continued)

FOREIGN PATENT DOCUMENTS

CN 1899687 A 7/2006
CN 101905166 12/2010
(Continued)

OTHER PUBLICATIONS

Leng et al., Efficacy of titanium dioxide compounds in preventing environmental contamination by meticillin resistant *Staphylococcus aureus* (MRSA), 2013, International Journal of Infection Control, v.9i:3, pp. 1-8 (Year: 2013).*
(Continued)

*Primary Examiner* — Kevin Joyner
*Assistant Examiner* — Holly M Mull
(74) *Attorney, Agent, or Firm* — Mintz Levin Cohn Ferris Glovsky and Popeo, P.C.

(57) ABSTRACT

Methods of reducing the incidence of healthcare-associated infections in various healthcare settings are provided. Methods for preventing or reducing the number of infections in a human or animal population are also provided. The methods as provided herein reduce the presence of various infectious agents that are commonly acquired or transmitted and are present on both animate and inanimate surfaces, including those infectious agents commonly found in healthcare settings. By reducing the presence of such infectious agents, the incidence of various types of infection or disease is thereby reduced.

18 Claims, 2 Drawing Sheets

Related U.S. Application Data

(60) Provisional application No. 62/015,596, filed on Jun. 23, 2014.

(51) Int. Cl.
    *B01J 35/00*     (2006.01)
    *B01J 35/02*     (2006.01)
    *B05D 1/04*     (2006.01)

(52) U.S. Cl.
    CPC .......... *B01J 35/0013* (2013.01); *B01J 35/023* (2013.01); *B05D 1/04* (2013.01); *A61L 2202/25* (2013.01)

(58) Field of Classification Search
    USPC .......................................................... 422/28
    See application file for complete search history.

(56) References Cited

U.S. PATENT DOCUMENTS

| | | |
|---|---|---|
| 6,589,912 B2 | 7/2003 | Kawai |
| 6,878,191 B2 | 4/2005 | Escaffre et al. |
| 8,609,121 B2 | 12/2013 | Averett et al. |
| 9,055,751 B2 | 6/2015 | Averett et al. |
| 9,144,242 B2 | 9/2015 | Averett et al. |
| 9,392,795 B2 | 7/2016 | Averett et al. |
| 2002/0096121 A1 | 7/2002 | Ingman et al. |
| 2002/0187082 A1 | 12/2002 | Wu et al. |
| 2003/0209501 A1 | 11/2003 | Leung |
| 2004/0060677 A1 | 4/2004 | Huang |
| 2005/0177957 A1* | 8/2005 | Long .................. D06M 13/005 8/115.51 |
| 2005/0191505 A1 | 9/2005 | Akarsu et al. |
| 2005/0214533 A1 | 9/2005 | Shimosaki et al. |
| 2006/0246149 A1 | 11/2006 | Bucholz et al. |
| 2008/0031832 A1 | 2/2008 | Wakefield et al. |
| 2008/0187457 A1 | 8/2008 | Mangiardi |
| 2009/0068089 A1 | 3/2009 | Hussain et al. |
| 2009/0104086 A1 | 4/2009 | Zax et al. |
| 2009/0110918 A1 | 4/2009 | Jacquiod et al. |
| 2009/0169425 A1 | 7/2009 | Park et al. |
| 2009/0241496 A1 | 10/2009 | Pintault et al. |
| 2010/0021710 A1 | 1/2010 | Hunt et al. |
| 2010/0119461 A1 | 5/2010 | Bicard-Benhamou et al. |
| 2010/0197495 A1 | 8/2010 | Filippini et al. |
| 2013/0180932 A1 | 7/2013 | Fukumura et al. |

FOREIGN PATENT DOCUMENTS

| | | |
|---|---|---|
| JP | 2001-286226 | 10/2001 |
| JP | 2001-314882 | 11/2001 |
| JP | 2005-040769 | 2/2005 |
| JP | 2006-321721 | 11/2006 |
| JP | 2009-084542 A | 4/2009 |
| KR | 2000009824 A | 2/2000 |
| KR | 20010048235 | 6/2001 |
| KR | 2005000389 | 1/2005 |
| WO | 2004/037301 A2 | 5/2004 |
| WO | 2007/026387 A2 | 3/2007 |
| WO | 2008/043396 A1 | 4/2008 |
| WO | 2008/135093 A1 | 11/2008 |
| WO | 2009030641 A1 | 3/2009 |
| WO | 2010/115720 A2 | 10/2010 |
| WO | 2011/033377 A2 | 3/2011 |

OTHER PUBLICATIONS

Kaoud, Removal of ammonia gas emission from broiler litter, Dec. 2013, Global Journal of Scientific Researches, vol. 1(2), pp. 42-47 (Year: 2013).*

Zou et al., "Zn- and La-modified $TiO_2$ photocatalysts for the isomerization of norbornadine to quadricyclane," Journal of Molecular Catalysis A: Chemical, vol. 286, Issues 1-2, pp. 63-69 (2008).

Zhao et al., "Zn-doped and $TiO_2$ nanoparticles with high photocatalytic activity synthesized by hydrogen-oxygen diffusion flame," Applied Catalysis B: Environmental, vol. 79, Issue 3, pp. 208-215 (2008).

Srinivasan et al., "Synergistic effects of sulfation and co-doping on the visible light photocatalysis of $TiO_2$," Journal of Alloys and Compounds, vol. 424, Issues 1-2, pp. 322-326 (2006).

Mar. 2, 2016 Office Action issued in Japanese Application No. 2014-509443 (with Partial English Translation).

Yao et al., "Photocatalytic disinfection of phytopathogenic bacteria by dye-sensitized $TiO_2$ thin film activated visible light," Surface and Coatings Technology (2007), 202(4-7), 1329-1332.

Cui et al., "Application of anatase $TiO_2$ sol derived from peroxotitannic acid in crop diseases control and regulation," Nanotech Conference & Expo 2009: An Interdisciplinary Forum on Nanotechnology, Biotechnology and Microtechnology, Houston, TX, United States, May 3-7, 2009 (2009), vol. 2, 286-289.

Zhang et al., "Photobiological effects of ano-$TiO_2$ semiconductors sol," Wuji Cailiao Xuebao (2008), 23(1), 55-60.

Yao et al., "Photocatalytic effects of $TiO_2$/Fe thin film with visible light on cellular surface ultrastructure and genomic DNA of bacteria," Surface and Coatings Technology (2007), 201(15), 6882-6885.

Kim et al., "Disinfection of Iceberg Lettuce by Titanium Dioxide-UV Photocatalytic Reaction," Journal of Food Protection, (Sep. 2009) vol. 72, No. 9, pp. 1916-1922.

Zhang et al., "Effects of nano-$TiO_2$ semiconductor sol on prevention from plant diseases," Nanoscience, (May 2007) vol. 12, No. 1, pp. 1-6.

International Search Report and Written Opinion, International Application No. PCT/US12/36337, dated Sep. 28, 2012.

Fujishima et al., "Electrochemical photolysis of water at a semiconductor electrode," Nature, vol. 238, pp. 37-38, 1972.

Chen et al., "Titanium Dioxide Nanomaterials: Synthesis, Properties, Modifications, and Applications," Chemical Reviews, vol. 107, pp. 2891-2959, 2007.

Matsunaga et al., "Photoelectrochemical sterilization of microbial cells by semiconductor powders," FEMS Microbiology Letters, vol. 29, pp. 211-214, 1985.

Tsuang et al., "Studies of photokilling of bacteria using titanium dioxide nanoparticles," Artificla Organs, vol. 32, pp. 167-174, 2008.

Choi et al., "Photocatalytic antibacterial effect of $TiO_2$ film on TiAg on *Streptococcus mutans*," Angle Orthodontist, vol. 79, pp. 528-532, 2009.

Dancer, S.J., "Importance of the environment in meticillin-resistant *Staphylococus aureus* acquisition: the case for hospital cleaning," Lancet Infectious Diseases, vol. 8, pp. 101-113, 2008.

Chen et al., Science Xpress, pp. 1-10, online publication Jan. 20, 2011, Science. 1200448.

Inada, K., "Actions spectra for photosynthesis in higher plants." Plant and Cell Physiology, vol. 17, pp. 355-365, 1976.

Matthews et al. "Photocatalytic Effect of Light-Activated Nanoscale Formulations of $TiO_2$ on Xanthomonas perforans and Control of Bacterial Spot of Tomato," Phytopathology vol. 103 pp. 228-236, 2013.

Teh et al., "Roles of titanium dioxide and ion-doped titanium dioxide on photocatalytic degradation of organic pollutants (phenolic compounds and dyes) in aqueous solutions: A review," Journal of Alloys and Compounds vol. 509 pp. 1648-1660, 2011.

Chen et al. "Investigation of transition metal ion doping behaviors on $TiO_2$ nanoparticles," J. Nanoparticle Research vol. 10 pp. 163-171 (2008).

Yuan et al, "Influence of co-doping of Zn(II) + (Fe(III) on the photocatalytic activity of $TiO_2$ for phenol degradation," Materials Chmistry and Physics vol. 73, pp. 323-326 2002.

Pelaez et al., "A Review on the Visible Light Active Titanium Dioxide Photocatalysts for Environmental Applications," Applied Catalysis B 125 (2012) 331-349.

GensNANO Self-Sanitizing Green Coating brochure, Green Earth Nano Science, Inc., May 2010.

Envirocare Webpage. http://www.altimategogreen.com. Accessed Jun. 3, 2016.

English translation of Document No. CN 1899687 A provided by espacenet.com: Description CN1899687.

U.S. Appl. No. 15/197,867, filed Jun. 30, 2016.

(56) References Cited

OTHER PUBLICATIONS

T.K. Giaorai et al., "Photocatalytic oxidation of organic dyes by nano-sized metal molybdate incorporated titanium dioxide photocatalysts", Journal of Molecular Catalysis A: Chemical, vol. 273, Issues 1-2, pp. 224-229 (2007).

* cited by examiner

REDUCTION OF INFECTIONS IN HEALTHCARE SETTINGS USING PHOTOCATALYTIC COMPOSITIONS

CROSS-REFERENCE TO RELATED APPLICATIONS

This application is a continuation of U.S. application Ser. No. 14/745,592, filed Jun. 22, 2015, which claims priority from U.S. Provisional Patent Application No. 62/015,596, filed Jun. 23, 2014; both of which are incorporated herein by reference in their entireties.

FIELD

The present disclosure relates to preventing and reducing the incidence of infectious agents found on a surface and particularly on surfaces found in healthcare settings.

BACKGROUND

Infectious agents found in and on building structures and surfaces of objects therein can lead to various health problems. Common offending infectious agents include microorganisms such as bacteria (e.g., gram negative rods such as *Escherichia coli* and gram-positive cocci such as *Staphylococcus aureus*). These and other bacteria can cause health problems such as dermal infections, respiratory infections, intestinal infections, and kidney disease. Also, pathogenic viruses such as influenza viruses are commonly found in buildings where they spread among those occupying the structure. Particularly, infectious agents within healthcare settings lead to healthcare-associated infections which, in turn, result in greater than a billion dollars in excess healthcare costs annually. These infections have created a challenge for healthcare management teams due to multi-drug resistant bacteria becoming commonplace in healthcare settings such as hospices, hospitals, and assisted-living or long-term care facilities.

Systems and methods designed to encourage, effect, monitor and enforce hand sanitation and other hygienic practices may aid in the reduction of the spread of infectious agents in healthcare settings, however, such measures alone are not sufficient. Thus, there remains a need for compositions and associated methods that prevent and reduce the presence of infectious agents in a variety of settings, including healthcare settings or facilities.

SUMMARY

According to one aspect, a method of reducing the incidence of healthcare-associated infections in a healthcare facility is provided. The method includes the step of treating at least one inanimate surface of the healthcare facility structure, or at least one object therein, or a combination thereof, with a photocatalytic composition. The photocatalytic composition comprises, consists essentially of, or consists of titanium dioxide ($TiO_2$) doped with zinc and at least one other doping agent.

According to one embodiment, the healthcare-associated infections susceptible to treatment include bone infection, joint infection, bloodstream infection, central nervous system infection, cardiovascular system infection, pneumonia, reproductive tract infection, and surgical site infection. According to another embodiment, the healthcare-associated infections susceptible to treatment include gastrointestinal infection, lower respiratory infection, upper respiratory infection, skin or soft tissue infection, bloodstream infection, eye infection, ear infection, nose infection, throat infection, mouth infection, and urinary tract infection.

The method is suitable for reducing the abundance in air and on surfaces of infectious agents including, but not limited to species of *Acinetobacter*, adenovirus, *Bacillus*, *Burkholderia*, *Bordetella*, *Brucella*, caliciviruses, herpes including zoster (chickenpox), *Clostridium*, corona viruses including SARS, MERS, and PEDV, *Enterococcus*, *Escherichia*, *Hemophilus*, hepatitis viruses A and B, influenza and parainfluenza viruses, *Klebsiella*, *Listeria*, *Legionella*, measles virus, mumps virus, *Mycobacterium*, *Neisseria*, norovirus, *Pseudomonas*, parvovirus, poliovirus, rhinovirus, respiratory syncytial virus, rotavirus, rubella, *Salmonella*, *Streptococcus*, *Staphylococcus*, and *Vibrio*. The infectious agents that are reduced include both those susceptible to antibiotics and, without limitation, those resistant to antibiotics such as MRSA (methicillin-resistant *Staphylococcus aureus*, VISA (vancomycin intermediate *Staphylococcus aureus*), MRE (multiply resistant *enterococci*), and VRE (vancomycin-resistant *enterococci*).

According to one embodiment, the photocatalytic composition is applied at a rate of from about 500 $ft^2$ per liter to about 1800 $ft^2$ per liter. According to one embodiment, the photocatalytic composition is applied by spraying, atomizing, coating, immersion, or dipping.

According to one embodiment, the incidence of healthcare-associated infections is reduced by at least 20% over a twelve month period after one treatment. According to another embodiment, the incidence of healthcare-associated infections is reduced by at least 30% over a twelve month period after one treatment.

According to one embodiment, the at least one inanimate surface of the healthcare facility structure includes any or all walls, fixtures, floors, and ceilings, including those parts of hallways, offices, bathrooms, elevators, stairwells, and kitchens/cafeterias, common areas, nurses' stations, and doctors' stations. According to one embodiment, the at least one object of the healthcare facility includes the curtains, call buttons, computers, monitors, wall computer kiosks, blood pressure cuffs, wheelchairs, lifts, carts, and beds.

According to one embodiment, the photocatalytic composition utilized in the methods provided herein comprises, consists essentially of, or consists of titanium dioxide that is doped with zinc and at least one other doping agent. According to one embodiment, the doping agent(s) increase the absorbance of light across the range of about 200 nm to about 500 nm. According to one embodiment, the absorbance of light of wavelengths longer than about 450 nm is less than 50% the absorbance of light of wavelengths shorter than about 350. According to one embodiment, the at least one other doping agent (i.e., in addition to zinc) can be one or more of Ag, Si, C, S, Fe, Mo, Ru, Cu, Os, Re, Rh, Sn, Pt, Li, Na, and K. According to one embodiment, the titanium dioxide nanoparticles have an average particle size of from about 2 nm to about 20 nm. According to one embodiment, the at least one other doping agent is silicon. According to one embodiment, the at least one other doping agent is silicon dioxide. According to one such embodiment, the photocatalytic composition exhibits a ratio of titanium dioxide to silicon dioxide of from about 3 to about 20. According to yet another embodiment, the photocatalytic composition exhibits a ratio of titanium dioxide to zinc from about 5 to about 150 and a ratio of titanium dioxide to silicon dioxide from about 1 to about 500. According to one embodiment, the photocatalytic composition comprises, consists essentially of, or consists of (A) about 5000 to about 10000 ppm of titanium dioxide, (B) about 50 to about 150 ppm of zinc, and (C) about 300 to about 1000 ppm of silicon dioxide.

According to another aspect, a method for preventing or reducing the number of infections in a human or animal population is provided. The method includes the step of treating inanimate surfaces of a structure occupied by the population, or at least one inanimate object present therein, or a combination thereof, with a photocatalytic composition. The photocatalytic composition comprises, consists essentially of, or consists of titanium dioxide doped with zinc and at least one other doping agent. According to one embodiment, the structure occupied by the population includes an agricultural facility, food-processing facility, catering facility, restaurants, hotel, motel, office, or childcare facility.

DETAILED DESCRIPTION

Figure 1:
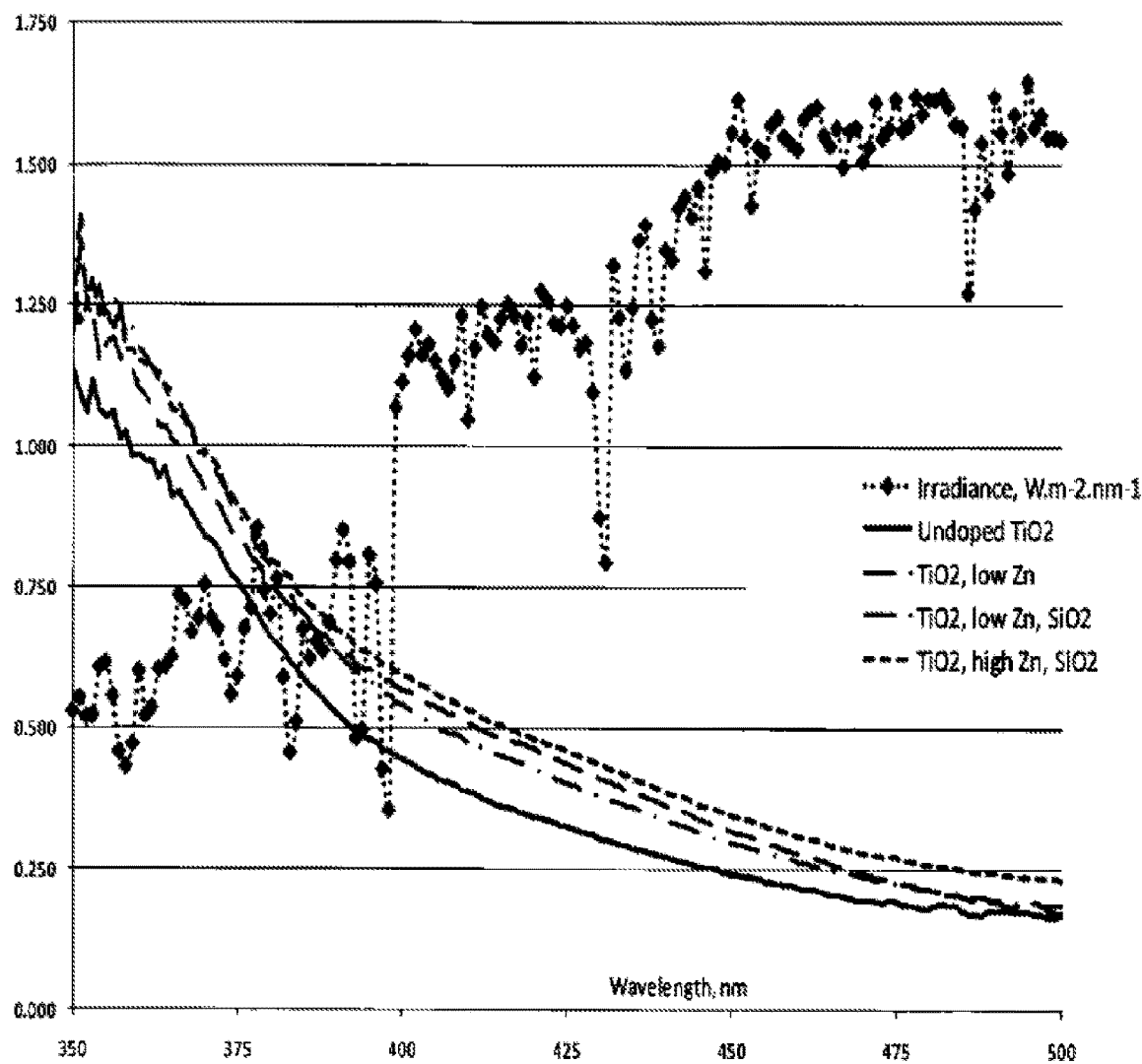
FIG. 1 is a graphic representation of solar energy capture of various $TiO_2$ compositions.

Methods of reducing the incidence of healthcare-associated infections in various healthcare settings are provided. Methods for preventing or reducing the number of infections in a human or animal population are also provided. The methods as provided herein reduce the abundance of various infectious agents that are commonly acquired or transmitted and are present on both animate and inanimate surfaces, including those infectious agents commonly found in healthcare settings. Further, airborne infectious agents also are reduced because such agents make contact with treated surfaces and are inactivated. By preventing and reducing the presence of such infectious agents, the incidence of various types of infection or disease is thereby reduced.

As used herein, the phrase, "at least one" means one or more and thus includes individual components as well as mixtures/combinations.

The term "comprising" (and its grammatical variations) as used herein is used in the inclusive sense of "having" or "including" and not in the exclusive sense of "consisting only of."

The terms "a" and "the" as used herein are understood to encompass the plural as well as the singular. The terms "doped" or "doping" as used herein are understood to encompass the introduction of one or more impurities (e.g., dopant, doping agent) into a material for the purpose of modifying the properties of the material.

The terms "treatment" and "treating" include mitigation of a pre-existing microbial disease or infestation by application or introduction of a photocatalytic composition as provided herein to an inanimate structure or object or an animate surface.

The terms "prevention" and "prophylaxis" include reduction of the incidence or severity of disease or infestation in either individuals or populations.

The term "healthcare-associated infection" as used herein refers to any localized or systemic condition resulting from an adverse reaction to the presence of an infectious agent (or its toxin) that was not present and without evidence of incubation at the time of admission to a healthcare setting.

The term "infectious agent" includes, but is not limited to, viruses, mold, and bacteria that cause or contribute to infection or disease in the human population Such organisms include but are not limited to species of *Acinetobacter*, adenovirus, *Bacillus, Burkholderia, Bordetella, Brucella*, caliciviruses, herpes including zoster (chickenpox), *Clostridium*, corona viruses including SARS, MERS, and PEDV, *Enterococcus, Escherichia, Hemophilus*, hepatitis viruses A and B, influenza and parainfluenza viruses, *Klebsiella, Listeria, Legionella*, measles virus, mumps virus, *Mycobacterium, Neisseria*, norovirus, *Pseudomonas*, parvovirus, poliovirus, rhinovirus, respiratory syncytial virus, rotavirus, rubella, *Salmonella, Streptococcus, Staphylococcus*, and *Vibrio*. The infectious agents that are reduced include both those susceptible to antibiotics and, without limitation, those resistant to antibiotics such as MRSA (methicillin-resistant *Staphylococcus aureus*, VISA (vancomycin intermediate *Staphylococcus aureus*), MRE (multiply resistant *enterococci*), and VRE (vancomycin-resistant *enterococci*).

Methods of reducing the incidence of healthcare-associated infections in various healthcare settings as described herein are provided. According to one embodiment, the method includes the step of treating at least one inanimate surface of the healthcare facility structure, the objects (e.g., medical equipment) therein, or a combination thereof with a photocatalytic composition as provided herein. Exemplary healthcare settings that include such structures and objects include, but are not limited to, hospitals, doctors' offices, elder or specialty care homes (e.g., assisted living, long-term care) and hospices. Exemplary structures of the facility subject to treatment include, but are not limited to, the walls, fixtures, floors, and ceilings, including those parts of hallways, offices, bathrooms, elevators, stairwells, and kitchens/cafeterias, common areas, nurses' stations, and doctors' stations. Exemplary inanimate objects in such a setting include the various equipment or medical devices that may be present including, but not limited to, curtains, call buttons, computers, monitors, wall computer kiosks, blood pressure cuffs, wheelchairs, lifts, carts, beds, and other similar objects.

According to one embodiment, healthcare-associated infections that can be acquired or transmitted in a healthcare setting and susceptible to treatment with the photocatalytic compositions provided herein include, but are not limited to, bone and joint infection (e.g., osteomyelitis, disc space infection, joint or bursa infection, prosthetic joint infection), bloodstream infection, central nervous system infection (e.g., intracranial infection, meningitis, or ventriculitis), cardiovascular system infection (e.g., myocarditis, pericarditis, endocarditis, mediastinitis, arterial or venous infection), Eye/ear/nose/throat/mouth infection (e.g., conjunctivitis, ear infection, oral infection, sinusitis, upper respiratory infection, pharyngitis, laryngitis, epiglottitis), gastrointestinal system infection (e.g., gastroenteritis, gastrointestinal tract infection, hepatitis, intraabdominal infection, necrotizing enterocolitis), lower respiratory infection (e.g., bronchitis, tracheobronchitis, tracheitis), pneumonia, reproductive tract infection (e.g., endometritis, episiotomy infection, vaginal cuff infection), surgical site infection, skin/soft tissue infection (e.g., breast abscess, mastitis, burn infection, circumcision infection, decubitus ulcer infection, infant pustulosis, skin infection, omphalitis), systemic infection, or urinary tract infection. According to a preferred embodiment, healthcare-associated infections that can be acquired or transmitted in a healthcare setting and are usceptible to treatment include gastrointestinal infection, lower respiratory infection, upper respiratory infection, skin or soft tissue infection, bloodstream infection, eye infection, ear infection, nose infection, throat infection, mouth infection, and urinary tract infection.

According to one embodiment, the incidence of healthcare-associated infections is reduced by at least 20% over a twelve month period after one treatment as provided herein. According to a preferred embodiment, the incidence of healthcare-associated infections is reduced by at least 30% over a twelve month period after one treatment as provided herein.

The compositions as provided herein may be applied in any known or suitable manner, including using application techniques such as spraying (e.g., electrostatic), atomizing, coating, immersion, or dipping. The best method of application may vary according to the nature of the surface to be coated. For many settings a preferred method is to use electrostatic spray, wherein droplets of the aqueous composition ranging in size from 5 micrometers to 100 micrometers are afforded a small electrical charge so that the droplets are attracted to the surface to be coated. In a further preferred technique, the coating is applied as a series of two to five spraying steps with drying allowed between each step. The photocatalytic coating can be applied at a rate of from about 500 ft$^2$ per liter to about 1500 ft$^2$ per liter.

According to yet another embodiment, a method for preventing or reducing the number of infections in a human or animal population is provided. The method includes treating inanimate structures used by the human or animal population, the inanimate objects that may be found within such structures, or a combination thereof, with a photocatalytic composition as provided herein. The step of treating the inanimate structures may include treating either a finished structure or a structure under construction. Exemplary settings that include such structures and objects include, but are not limited to, agricultural facilities, food-processing facilities, catering facilities, restaurants, hotels, motels, and childcare facilities. Exemplary parts of the structures that can be treated include, but are not limited to, walls, fixtures, floors, and ceilings, including those parts of hallways, offices, bathrooms, elevators, stairwells, and kitchens.

The methods as provided herein utilize photocatalytic compositions that include titanium dioxide ($TiO_2$) nanoparticles, which are useful in the prevention and reduction of infectious agents found on a surface and particularly useful in the reduction of healthcare-associated infections. The photocatalytic compositions as provided herein, including any nanoparticles therein, are free of any polymer or polymer composition (e.g., polymer-stabilized inorganic composition). The photocatalytic compositions as provided herein can be used to treat both animate and inanimate surfaces in a variety of environments where an infectious agent is located. The photocatalytic compositions provided herein contain only well characterized and safe materials, can be easily applied to surfaces using ordinary spray equipment, exhibit photocatalytic activity, and are effective in settings of low UV irradiance, including interior artificial lighting.

According to one embodiment, the methods as provided herein utilize photocatalytic compositions that comprise, consist essentially of, or consist of titanium dioxide ($TiO_2$) doped with zinc and at least one other doping agent. Doping agents suitable in the photocatalytic compositions provided herein, in addition to zinc, include Ag, Si, C, S, Fe, Mo, Ru, Cu, Os, Re, Rh, Sn, Pt, Li, Na, and K, and combinations thereof. Particularly preferred doping agents include zinc and silicon.

According to one embodiment, the composition comprises, consists essentially of, or consists of titanium dioxide doped with zinc and the ratio of titanium dioxide to zinc is from about 5 to about 150. According to a preferred embodiment, the ratio of titanium dioxide to zinc is from about 40 to about 100. The photocatalytic composition can further comprise, consist essentially of, or consist of silicon dioxide ($SiO_2$). According to such an embodiment, the ratio of titanium dioxide to silicon dioxide can range from about 1 to about 500. According to a preferred embodiment, the ratio of titanium dioxide to silicon dioxide is from about 3 to about 20. According to one embodiment, the titanium dioxide nanoparticles as provided herein have an average particle size of from about 2 nm to about 20 nm.

According to a preferred embodiment, the photocatalytic composition as provided herein comprises, consists essentially of, or consists of from about 5000 to about 10000 ppm of titanium dioxide, from about 50 to about 150 ppm of zinc, and from about 300 to about 1000 ppm of silicon dioxide. According to one embodiment, the photocatalytic composition as provided herein absorbs electromagnetic radiation in a wavelength range of from about 200 nm to about 500 nm. According to one embodiment, the absorbance of light of wavelengths longer than about 450 nm is less than 50% the absorbance of light of wavelengths shorter than about 350 nm.

The invention will be further understood by the following examples, which are intended to be illustrative of the invention, but not limiting thereof.

EXAMPLE 1

Absorption characteristics of nanoscale $TiO_2$ were compared to nanoscale $TiO_2$ doped with two differing zinc levels and $SiO_2$, over the wavelength range of 350 nm to 500 nm. The nanoparticle compositions were manufactured by a modified sol-gel process, to produce formulations containing nanoparticles of anatase $TiO_2$ whose average size was 6 to 7 nm. Zinc was incorporated as a doping agent to provide either low zinc content (0.125% relative to $TiO_2$) or high zinc content (1.25% relative to $TiO_2$). When $SiO_2$ was an additional dopant, it was present at 10% relative to $TiO_2$. The preparations were dried and absorbance was measured using standard methods for obtaining diffuse reflectance spectra (DRS) of powders. The solar irradiance (hemispherical, 37 degree tilt) from ASTM G173-03 across this spectral range is shown for reference, (See FIG. 1).

It is evident upon inspection that the $TiO_2$ preparations doped with hetero-atoms absorb more strongly than otherwise similar undoped $TiO_2$ in the near-UV and violet region of the spectrum. The doped preparations absorb 25 to 35 percent more of the energy available from 400 to 450 nm, a region of the spectrum that is present in typical interior light as well as sunlight.

EXAMPLE 2

Photocatalytic Activity of Various Formulations of $TiO_2$ Doped with Zn and $SiO_2$ Under UV Illumination The four formulations described in Example 1 were tested for their photocatalytic activity in a standardized system. Each preparation was suspended in water at approximately 8000 ppm and applied to a glass panel using a robotic high volume low pressure sprayer, and allowed to dry for 24 hours. These panels were each attached to a glass tube to form a container, into which was placed 30 ml of an aqueous solution of methylene blue at a concentration providing an optical density of 2.3 at 664 nm. The tubes were covered with a glass panel and subjected to illumination at an energy density of approximately 0.5 mW/cm$^2$ from a lamp (GE item F18T8/BLB) affording ultraviolet illumination at 354 nm. This lamp provides no light at wavelengths below 300 nm or above 400 nm. The optical density of the methylene blue solution in each sample was monitored over a period of 48 hours and is shown in FIG. 2.

Figure 2:
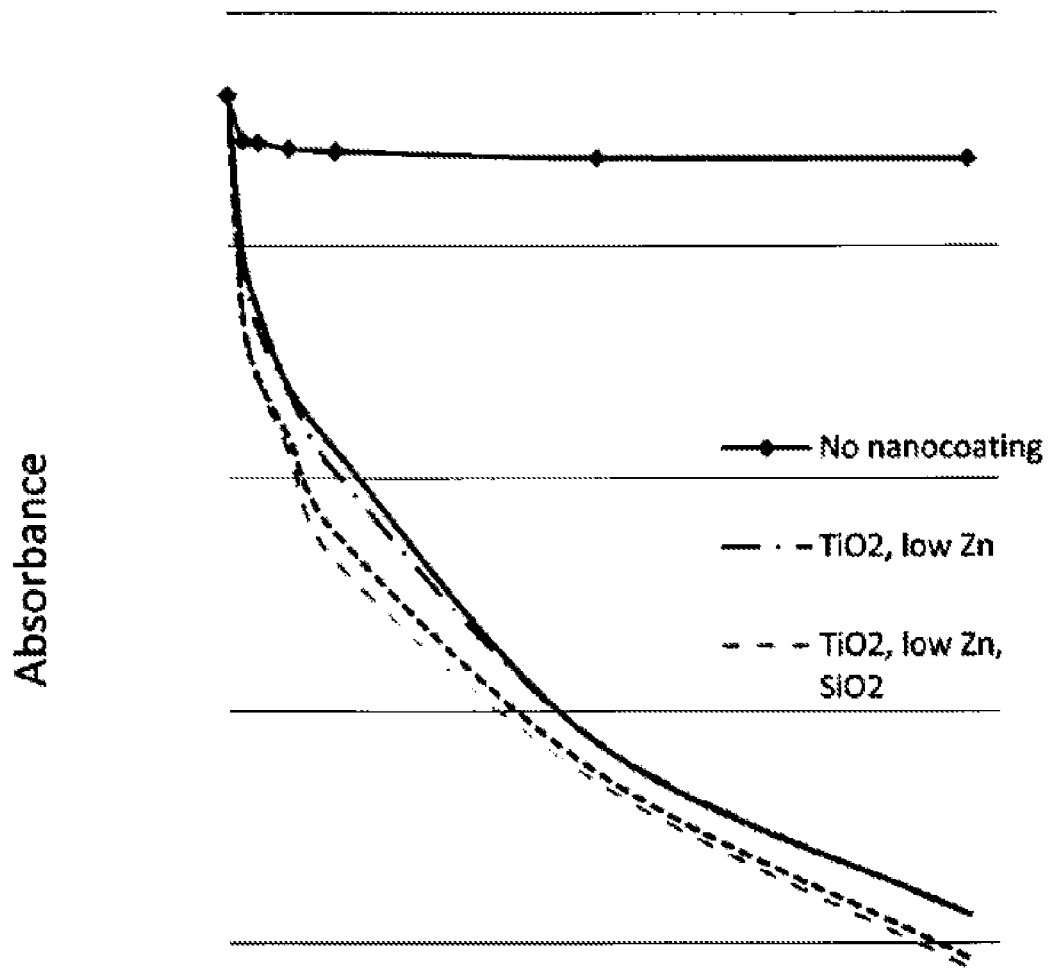
FIG. 2 is a graphic representation of the photocatalytic activity of various $TiO_2$ compositions when irradiated at 354 nm.

FIG. 2 shows that the nanocoatings caused a decline in optical density, which results from photocatalytic degradation of the organic dye methylene blue. The coatings that had the higher amounts of dopants afforded the most rapid declines, consistent with greater absorbance of light from the lamp in the UV range (354 nm).

EXAMPLE 3

Photocatalytic Activity of Various Formulations of TiO$_2$ Doped with Zn and SiO$_2$ Under Visible Light Illumination The four formulations described in Example 1 were tested for their photocatalytic activity in a second system, in which the experimental illumination was changed to more closely mimic relevant illumination such as daylight or interior light, which are deficient in the ultraviolet energy used in Example 2. Also, for this example the nanoparticle formulations were evaluated as colloidal suspensions in 20 mM phosphate buffer, pH 7.2, rather than on a static surface. The experiment was performed in a 96-well plate format, in which each well contained methylene blue (observed OD$_{655}$ ranging from 0.05 to 0.5) and a nanoparticle formulation or appropriate controls in a final volume of 200 microliters. The plate was illuminated from a distance of 20 cm with light from two Sylvania Gro-Lux lamps (F20 T12 GRO/AQ). These lamps emit only 2% of their total emitted energy below 400 nm, whereas approximately 36% of their total energy is emitted between 380 and 500 nm, with a peak at 436 nm (reference: Technical Information Bulletin "Spectral Power Distributions of Sylvania Fluorescent Lamps", Osram Sylvania, www.sylvania.com).

The compositions of the four preparations tested in this experiment were independently verified by the analytical technique known as ICP-AES (inductively coupled plasma atomic emission spectrometry), which demonstrated their equivalent TiO$_2$ content and variations in Si and Zn composition as described in Example 1. The nanoparticle preparations were diluted in buffer to provide final concentrations of 75 ppm of titanium dioxide of each formulation, with twenty replicate wells of each formulation. After a short period of equilibration in the dark, each plate was exposed to illumination with shaking, and optical density at 655 nm was measured at multiple times over using a Molecular Devices SpectraMax Plus spectrophotometer. The observed linear declines in optical density due to each formulation were measured to give the rates summarized in Table 1.

TABLE 1

| | Trial 1 | Trial 2 |
|---|---|---|
| TiO$_2$, low Zn | 0.0017* | 0.0016 |
| TiO$_2$, low Zn, high Si | 0.0020 | Not tested |
| TiO$_2$, high Zn, high Si | 0.0019 | Not tested |
| TiO$_2$ only | Not tested | 0.0013 |

*All values reported are the decline in optical density at 655 nm, per minute

It is evident that all the doped TiO$_2$ formulations show significantly increased rates (25% to 50%) compared to the undoped TiO$_2$ formulation. The magnitude of the increase in the rate of photocatalytic activity is highly consistent with the increased absorption of light energy in the range of 400 nm to 450 nm that is evident in the spectra described in Example 1.

EXAMPLE 4

Infections in a long term acute care healthcare facility were evaluated upon treatment with a photocatalytic composition as provided herein. The results show that the typical infections arising in a healthcare facility may be significantly reduced as a result of such treatment.

A photocatalytic composition including titanium dioxide nanoparticles doped with zinc and silicon dioxide was prepared. The individual nanoparticles were approximately six to ten nanometers in dimension, and were dispersed in water to provide about 8000 ppm TiO$_2$, about 100 ppm Zn, and about 500 ppm SiO$_2$. This dispersed colloidal suspension of doped nanoparticles was used to coat essentially all accessible surfaces in a 42 bed health care facility that provides long term acute care services to patients after surgery and other medical procedures.

The coating was applied using the following procedure. Vacant rooms and bathrooms were thoroughly cleaned by housekeeping staff, including removal of all linens and surface disinfection according to institutional procedures. The photocatalytic coating was then applied using electrostatic spray at a rate of about 1200 ft$^2$ per liter. All objects in the room were coated, including both hard and soft surface furniture and nearby walls, window and privacy curtains, and equipment such as call buttons and remote controls. Bathroom walls, fixtures, and floors were specifically coated. A minimum of 15 minutes was allowed for drying of coated surfaces, after which the room was ready for occupancy. In addition to patient rooms, all common areas, including hallways, offices, visitor restrooms, elevators, stairwells, kitchen, and nurse's stations (including computers) were coated. Equipment was also coated, including wall computer kiosks, blood pressure cuffs, wheelchairs, lifts, carts, and other similar surfaces.

The healthcare facility made no changes to institutional infection control processes or procedures. The number of infections were recorded in compliance with existing institutional protocols. Table 2 reports the number of infections occurring in each quarter of the year following treatment, compared with the number of infections at the same institution during the same quarter of the year prior to treatment. Infections were fewer in every quarter after treatment than in any quarter prior to treatment. When summed over the entire assessment period, infections declined 40% in the year following surface coating with the photocatalytic composition.

TABLE 2

| | Infections per three month period | |
|---|---|---|
| | Year Before Coating | Year After Coating |
| Q1 | 17 | 8 |
| Q2 | 15 | 7 |
| Q3 | 16 | 11 |
| Q4 | 12 | 6 |

EXAMPLE 5

The composition described in Example 4 was applied using the procedure described in Example 4 to a 250 bed health care facility that provides sub-acute long term residential care. Similar to Example 4, no change was made to institutional processes or procedures, and infections occurring in the facility were enumerated in accord with standard protocols. Table 3 reports the number of infections occurring in each quarter of the year following treatment, compared with the number of infections at the same institution during the same quarter of the year prior to treatment. Infections were fewer in every quarter after treatment compared to any quarter prior to treatment. When summed over the entire assessment period, infections declined 32% in the year following surface coating with the photocatalytic composition.

TABLE 3

| | Infections per three month period | |
|---|---|---|
| | Year Before Coating | Year After Coating |
| Q1 | 78 | 50 |
| Q2 | 73 | 52 |
| Q3 | 58 | 42 |
| Q4 | 66 | 41 |

The larger size of this facility allowed an examination of selected categories of infections, as defined by the USA Centers for Disease Control (CDC), because of the larger total number of events. For this evaluation, the absolute numbers of infections and the actual patient population were used to calculate the rate of each infection for each month of the evaluation interval. The rates were reported in the unit of events per 1000 patient days. These monthly rates were averaged for the year before application of the coating and the year after application, and compared.

The results are shown in Table 4, below, along with the results of a two-tailed homoscedastic t-test. The decline in total of all infection rates was statistically significant. Six of the seven infection categories that were monitored showed a decline in their average rates. However, not all infection categories were equally affected. Also, because the statistical test did not presume the direction of change that might occur, the p-values were suggestive but not conclusive that the observed results did not occur by chance.

TABLE 4

| Type of Infection | 12 months before | 12 months after | p value |
|---|---|---|---|
| Gastrointestinal | 0.358 | 0.333 | 0.858 |
| Skin and Soft Tissue | 1.017 | 0.767 | 0.192 |
| Bloodstream | 0.033 | 0.017 | 0.557 |
| Eye, Ear, Nose, Throat, or Mouth | 0.708 | 0.367 | 0.108 |
| Urinary Tract | 1.683 | 1.025 | 0.079 |
| Upper Respiratory | 0.217 | 0.050 | 0.219 |
| Lower Respiratory | 0.533 | 0.648 | 0.536 |
| TOTAL | 4.567 | 3.225 | 0.016 |

To strengthen the statistical analysis, additional data was included in a subsequent analysis, and is shown in Table 5 below, along with the results of a two-tailed homoscastic t-test. As before, results for the grouped infections of all types were statistically significantly different. Six of the seven individual infection categories that were monitored showed a decline in the average rate of occurance. However, the one infection category that showed an increase changed from lower respiratory to blood stream. It is likely that such shifts are a result of the relatively low number of events overall, and that larger studies are needed to define the full range of benefit. Nevertheless, five of the seven categories showed a decline in both analyses. This analysis also strengthened the statistical evidence for a non-chance reduction in eye, ear, nose throat or mouth infection (EENT), urinary tract infections (UTI), and upper respiratory infections (URI), with both EENT and UTI achieving formal statistical significance ($p<0.05$).

TABLE 5

| Type of Infection | 12 months before | 17 months after | p value |
|---|---|---|---|
| Gastrointestinal | 0.358 | 0.300 | 0.626 |
| Skin and Soft Tissue | 1.017 | 0.911 | 0.538 |
| Bloodstream | 0.033 | 0.044 | 0.764 |
| Eye, Ear, Nose, Throat, or Mouth | 0.708 | 0.350 | 0.043 |
| Urinary Tract | 1.683 | 0.978 | 0.027 |
| Upper Respiratory | 0.217 | 0.058 | 0.158 |
| Lower Respiratory | 0.533 | 0.499 | 0.836 |
| TOTAL | 4.567 | 3.172 | 0.004 |

It is important to note that the construction and arrangement of the methods and steps shown in the exemplary embodiments is illustrative only. Although only a few embodiments of the present disclosure have been described in detail, those skilled in the art will readily appreciate that many modifications are possible without materially departing from the novel teachings and advantages of the subject matter recited in the claims. Accordingly, all such modifications are intended to be included within the scope of the present disclosure as defined in the appended claims. The order or sequence of any process or method steps may be varied or re-sequenced according to alternative embodiments. Other substitution, modification, changes and omissions may be made in the design, operating conditions and arrangement of the embodiments without departing from the spirit of the present disclosure as expressed in the appended claims.

All publications, patents and patent applications cited in this specification are herein incorporated by reference, and for any and all purposes, as if each individual publication, patent or patent application were specifically and individually indicated to be incorporated by reference. In this case of inconsistencies, the present disclosure will prevail.

We claim:

1. A method of reducing the incidence of healthcare-associated infections among patients in a facility structure, comprising:
   treating at least one inanimate surface of the facility structure, or at least one object therein, or a combination thereof, with a photocatalytic composition comprising titanium dioxide ($TiO_2$) nanoparticles doped with zinc and at least one other doping agent;
   wherein the at least one other doping agent is silicon or silicon dioxide;
   wherein the healthcare-associated infection is selected from the group consisting of bone infection, joint infection, bloodstream infection, central nervous system infection, cardiovascular system infection, pneumonia, reproductive tract infection, surgical site infection, gastrointestinal infection, lower respiratory infection, upper respiratory infection, skin or soft tissue infection, bloodstream infection, eye infection, ear infection, nose infection, throat infection, mouth infection, and urinary tract infection;

wherein the photocatalytic composition is applied at a rate of from about 500 ft$^2$ per liter to about 1500 ft$^2$ per liter; and, wherein the incidence of healthcare-associated infections is reduced by at least 20% over a twelve month period after one treatment of the inanimate surfaces of the facility structure, at least one object therein, or a combination thereof.

2. The method of claim 1, wherein the facility structure is a healthcare facility structure.

3. The method of claim 1, wherein the photocatalytic composition is applied by spraying, atomizing, coating, immersion, or dipping.

4. The method of claim 1, wherein the at least one inanimate surface includes walls, fixtures, floors, and ceilings of hallways, offices, bathrooms, elevators, stairwells, kitchens/cafeterias, common areas, nurses' stations, and doctors' stations.

5. The method of claim 1, wherein the at least one object is selected from the group consisting of curtains, call buttons, computers, monitors, wall computer kiosks, blood pressure cuffs, wheelchairs, lifts, carts, and beds.

6. The method of claim 1, wherein the at least one other doping agent increases the absorbance of light across the range of about 200 nm to about 500 nm.

7. The method of claim 1, wherein the absorbance of light of wavelengths longer than about 450 nm is less than 50% the absorbance of light of wavelengths shorter than about 350.

8. The method of claim 1, wherein the titanium dioxide nanoparticles have an average particle size of from about 2 nm to about 20 nm.

9. The method of claim 1, wherein the at least one other doping agent is silicon.

10. The method of claim 1, wherein the at least one other doping agent is silicon dioxide.

11. The method of claim 10, the photocatalytic composition having a ratio of titanium dioxide to silicon dioxide of from about 3 to about 20.

12. The method of claim 10, the photocatalytic composition having a ratio of titanium dioxide to zinc from about 5 to about 150 and a ratio of titanium dioxide to silicon dioxide from about 1 to about 500.

13. The method of claim 1, wherein the photocatalytic composition consists essentially of:
(A) about 5000 to about 10000 ppm of titanium dioxide,
(B) about 50 to about 150 ppm of zinc, and
(C) about 300 to about 1000 ppm of silicon dioxide.

14. A method for preventing or reducing the number of infections in a human or animal population, comprising:
treating at least one inanimate surface of a structure occupied by the population, or at least one inanimate object present therein, or a combination thereof, with a photocatalytic composition comprising titanium dioxide (TiO$_2$) nanoparticles doped with zinc and at least one other doping agent;
wherein the structure occupied by the population is selected from the group consisting of an agricultural facility, food-processing facility, catering facility, restaurants, hotel, motel, and childcare facility;
wherein the incidence of infections is reduced by at least 20% over a twelve month period after one treatment of the inanimate surfaces of the structure, at least one object therein, or a combination thereof.

15. The method of claim 14, wherein the incidence of infections is reduced by at least 30% over a twelve month period after one treatment of the inanimate surfaces of the structure, or at least one object therein, or a combination thereof.

16. The method of claim 14, wherein the step of treating inanimate surfaces of the structure, or at least one object therein, or a combination thereof, prevents and reduces the presence at least one infectious agent selected from the group consisting of species of *Acinetobacter, adenovirus, Bacillus, Burkholderia, Bordetella, Brucella, caliciviruses, herpes including zoster* (chickenpox), *Clostridium*, corona viruses including SARS, MERS, and PEDV, *Enterococcus, Escherichia, Hemophilus, hepatitis* viruses A and B, *influenza* and *parainfluenza* viruses, *Klebsiella, Listeria, Legionella*, measles virus, mumps virus, *Mycobacterium, Neisseria, norovirus, Pseudomonas, parvovirus, poliovirus, rhinovirus, respiratory syncyticia* virus, *rotavirus, rubella, Salmonella, Streptococcus, Staphylococcus, Vibrio*, MRSA (methicillin-resistant *Staphylococcus aureus*, VISA (vancomycin intermediate *Staphylococcus aureus*), MRE (multiply resistant *enterococci*), and VRE (vancomycin-resistant *enterococci*)).

17. The method of claim 14, wherein the at least one other doping agent is silicon.

18. The method of claim 14, wherein the at least one other doping agent is silicon dioxide.

* * * * *